(12) United States Patent
Steier

(10) Patent No.: US 11,033,738 B2
(45) Date of Patent: Jun. 15, 2021

(54) APPARATUS FOR TREATMENT OF SNORING AND SLEEP APNOEA

(71) Applicants: KING'S COLLEGE LONDON, London (GB); GUY'S AND ST. THOMAS' NHS FOUNDATION TRUST, London (GB)

(72) Inventor: Joerg Sebastien Steier, London (GB)

(73) Assignees: KING'S COLLEGE LONDON, London (GB); GUY'S AND ST. THOMAS' NHS FOUNDATION TRUST, London (GB)

( * ) Notice: Subject to any disclaimer, the term of this patent is extended or adjusted under 35 U.S.C. 154(b) by 226 days.

(21) Appl. No.: 15/540,522

(22) PCT Filed: Feb. 5, 2016

(86) PCT No.: PCT/EP2016/052503
§ 371 (c)(1),
(2) Date: Jun. 28, 2017

(87) PCT Pub. No.: WO2016/124739
PCT Pub. Date: Aug. 11, 2016

(65) Prior Publication Data
US 2017/0368337 A1    Dec. 28, 2017

(30) Foreign Application Priority Data

Feb. 6, 2015    (GB) ..................... 1501983

(51) Int. Cl.
*A61N 1/36*    (2006.01)
*A61N 1/04*    (2006.01)

(52) U.S. Cl.
CPC ......... *A61N 1/3601* (2013.01); *A61N 1/0408* (2013.01); *A61N 1/0476* (2013.01); *A61N 1/36034* (2017.08)

(58) Field of Classification Search
CPC .............. A61N 1/3601; A61N 1/36034; A61N 1/36014; A61N 1/3611; A61N 1/0408; A61N 1/0476
See application file for complete search history.

(56) References Cited

U.S. PATENT DOCUMENTS 5,123,425 A * 6/1992 Shannon, Jr. .......... A61B 5/113
    128/848
5,190,053 A * 3/1993 Meer .................... A61N 1/0548
    600/529

(Continued)

FOREIGN PATENT DOCUMENTS

| CN | 102119043 | 7/2011 |
| CN | 102686271 | 9/2012 |

(Continued)

OTHER PUBLICATIONS

Medtronic Respond II Neuromuscular Stimulator parameter and specifications list, https://www.dotmed.com/listing/nerve-stimulator/medtronic/respond-ii-3108-neuromuscular/2391775 (Year: 2019).*

(Continued)

*Primary Examiner* — Eric D. Bertram
(74) *Attorney, Agent, or Firm* — Casimir Jones, SC; Robert A. Goetz

(57) ABSTRACT

A portable, battery powered apparatus (10) generates an electrical signal between electrodes (15a, 15b) to be applied to the skin of a patient for reduction or prevention of snoring or obstructive sleep apnoea. The signal comprises electrical stimulation at a frequency of 1-100 Hz and the signal comprises a stimulation free period of at least 0.5 seconds every 20 seconds, avoiding muscle fatigue when used for long periods, e.g. overnight.

19 Claims, 4 Drawing Sheets

(56) References Cited

U.S. PATENT DOCUMENTS

| | | | |
|---|---|---|---|
| 6,021,352 A * | 2/2000 | Christopherson | A61N 1/3601 607/42 |
| 6,240,316 B1 * | 5/2001 | Richmond | A61N 1/3601 607/42 |
| 6,251,126 B1 * | 6/2001 | Ottenhoff | A61N 1/36007 607/42 |
| 6,269,269 B1 * | 7/2001 | Ottenhoff | A61N 1/3601 607/42 |
| 8,160,712 B1 | 4/2012 | Freed | |
| 8,428,725 B2 * | 4/2013 | Meadows | A61B 5/4818 607/42 |
| 2009/0210032 A1 | 8/2009 | Beiski | |
| 2012/0232611 A1 | 9/2012 | Sasaki | |

FOREIGN PATENT DOCUMENTS

| | | |
|---|---|---|
| CN | 103055417 | 4/2013 |
| GB | 2500641 | 10/2013 |
| JP | 5636129 | 12/2014 |
| WO | 92/03983 | 3/1992 |
| WO | 92/15364 | 9/1992 |
| WO | 97/49455 | 12/1997 |
| WO | 2006/008741 | 1/2006 |
| WO | 2006/054359 | 5/2006 |
| WO | 2009/048580 | 4/2009 |

OTHER PUBLICATIONS

International Search Report, International Patent Application No. PCT/EP2016/052503, dated May 24, 2016.

International Preliminary Report on Patentability, International Patent Application No. PCT/EP2016/052503, dated Jan. 25, 2017.

Search Report, GB Application No. 1501983.9, dated Jun. 25, 2015.

Steier, Joerg, John Seymour, Gerrard F. Rafferty, Caroline J. Jolley, Eskinder Solomon, Yuanming Luo, William D-C, Man, Michael I. Polkey, and John Moxham. "Continuous transcutaneous submental electrical stimulation in obstructive sleep apnea: a feasibility study" Chest 140, No. 4 (2011): 998-1007.

Hida, Wataru, Shinichi Okabe, Hiroshi Miki, Yoshihiro Kikuchi, Osamu Taguchi, Tamotsu Takishima, and Kunio Shirato. "Effects of submental stimulation for several consecutive nights in patients with obstructive sleep apnoea." Thorax 49, No. 5 (1994): 446-452.

English translation of Japanese Office Action No. 2017-541369, dated Sep. 4, 2019, 4 pages.

* cited by examiner

APPARATUS FOR TREATMENT OF SNORING AND SLEEP APNOEA

INTRODUCTION

The present invention relates to the treatment or prevention of snoring and/or a related condition such as obstructive sleep apnoea, and to apparatus and methods therefor.

BACKGROUND TO THE INVENTION

Snoring during sleep can be a nuisance to both the snorer and anyone else in the vicinity. For the snorer, it can result in lack of sleep and may be a sign or warning of a more serious condition, especially obstructive sleep apnoea.

Known treatments for snoring revolve around clearing a blockage in the breathing passage. Sufferers may be advised to lose weight, stop smoking or limit alcohol intake. Nasal sprays, nasal strips and nose clips, as well as mandibular advancement devices, can be used to reduce snoring.

In more serious cases, a continuous positive airway pressure (CPAP) machine is often used to control sleep apnoea and the snoring associated with it. Known such devices pump a controlled stream of air through a flexible hose to a mask worn over the nose and/or mouth.

Surgery is also available as a method of correcting snoring. These procedures are quite invasive, however, and there are risks of adverse side effects.

Electrical devices to be worn on the body or at least attached to the neck or throat are also known. US 2008/0021506 describes a device with pads disposed above the laryngeal muscles of a patient. It generates electronic impulses to provide continuous contraction of tongue muscles, with in particular 5-10 pulses per second, though few other details are given and the device appears not to have been tested.

Another device, described in US 2009/0216293, also stimulates the patient with an electrical signal comprising positive and negative electric pulses at a frequency of about 2.7 kHz, with a variable output signal. Again, few details of actual signals used successfully are given, suggesting this device too has not been properly tested on humans, if at all.

A known study investigated the effect of directly stimulating the hypoglossal nerve, to induce throat/tongue muscle tensioning and treat obstructive sleep apnoea, though using an implanted device (Strollo et al, N Engl J Med 2014; 370:139-149, Jan. 9, 2014).

Other treatment strategies include monitoring for snoring or sleep apnoea indicators, then providing stimulation triggered by those indicators. These require sophisticated monitoring, usually with the patient attached by wires to a machine, and are less suitable for home use or cannot be provided in portable formats.

GB 2500641 describes a mains-powered stimulation device for use on the feet and legs, not disclosed as useful for sleep disorders; it applies a stimulation, e.g. to increase venous blood flow in the leg, with a rest period to allow the leg muscle to recover.

U.S. Pat. No. 8,160,712 describes a device that applies stimulation to the intercostal muscles. The stimulation is pulsed with a rest period of 4 seconds every 59 seconds.

A further device, known from WO 97/49455, applies stimulation to treat sleep apnoea, with a continuous signal. WO 92/03983 describes a still further device that appears to operate in response to a sleep apnoea episode and then apply pulsed stimulation to the sufferer. In both cases, detection of the sleep apnoea episode is required and thus the application of the pattern of stimulation is not continuous throughout the night.

WO 2006/008741, WO 92/15364 and WO 2009/048580 describe related devices and were found in prior art searching but are not believed of relevance to the invention.

There exists thus a need for alternative or improved devices that will reduce or prevent snoring, and/or reduce or prevent more serious, related conditions such as sleep apnoea. These devices should preferably be suitable to be worn by a patient for long periods, e.g. overnight, so that effective and relaxing sleep can be enjoyed. These devices are preferably lightweight and portable.

SUMMARY OF THE INVENTION

Accordingly, the invention provides an apparatus for reducing or preventing snoring or sleep apnoea, i.e. for treatment of these conditions. Embodiments of the apparatus are small, lightweight and portable, and can be battery powered, providing devices that can be worn comfortably by a patient for hours, e.g. overnight, for the whole duration of normal sleep.

An apparatus of the invention generally comprises
a pair of electrodes, and
a power supply that generates an electrical signal between the electrodes, wherein the signal has a frequency of 1-100 Hz and is discontinuous so as to provide for continuous treatment without muscle fatigue.

An advantage of the invention is that the signal is discontinuous. It has been found that this facilitates provision of effective treatment without fatigue, e.g. of the patient's tongue muscle or muscles such that the treatment fails to be effective, hence without fatigue e.g. of the patient's response to the treatment such that its usefulness diminishes over the time period of normal sleep. Recovery of physiological processes during the discontinuous phase, when there is no signal (even though the absence of signal is relatively brief) means the treatment works over a long time period, essentially continuously in the context of normal sleep. Previous devices failed in this respect and research was theoretical and did not provide devices or treatments that would remain effective overnight.

A further advantage is that the signal is mild enough not to significantly disturb or prevent sleep but strong enough to elicit a contraction of the tongue muscle (genioglossus) that reduces snoring or sleep apnoea.

It is preferred that the apparatus provides said continuous treatment over a period of 3 hours or more, 4 hours or more, 5 hours or more, 7 hours or more, or longer still. The treatment is thus preferably continuous in the context of the period of time, many hours, of normal sleep as the apparatus periodically delivers a signal while it is turned on. The apparatus does not monitor or detect snoring or sleep apnoea; it generates the signal continuously, with the discontinuous phase (also described as a stimulation free period) as described, until turned off.

The signal may comprise a stimulation free period of at least 0.5 seconds, preferably at least 1 second, every 20 seconds or a stimulation free period of at least 0.5 seconds, optionally at least 1 second, every 10 seconds. The ratio of the stimulation free period to the period when a signal is delivered is referred to as duty cycle, hence a duty cycle of 50%, used in some tested embodiments of the invention, indicates equal periods with and without signal. Within a time period of up to 30 seconds, preferably up to 20 seconds, a duty cycle is suitably 5-95%, more suitably 10-90% or 20-80%. In apparatus tested to date, good treatment has been obtained with an approximate 50% duty cycle over 10 seconds. The signal is hence discontinuous in the context of 20 or 30 seconds or so, in which time the signal is off for a minimum period and on for a minimum period.

Variation in signal frequency affects muscle contraction force. We have found that a suitable frequency, to achieve appropriate contraction, enough to treat snoring or apnoea in a sleeping patient, falls within a broad range as indicated above, and is more suitably 5-60 Hz or 10-50 Hz. In equipment made and tested, a frequency range of 20-40 Hz was included and this was found effective across the range. In specific embodiments the frequency is 30+/−2 Hz. Different combinations of signal parameters tend to suit different patients according to age and weight and facial hair, and other factors, so a device set up to operate over a range of parameters, capable of delivering signals with a range of strengths, will accommodate most patients and possibly everyone.

The signal current can be varied as well (usually achieved by variation in voltage across the electrodes), especially for different patients and optionally in conjunction with variation in signal frequency. Current in the range up to 40 mA, especially up to 30 mA, has been used successfully and in general most patients can be accommodated with a current in the range of, or varying from, 1 to 20 mA. Both these parameters can be varied independently; as one specific example a current of about 10 mA with signal frequency of about 30 Hz worked well in a patient. Typically, the apparatus uses a lower current for a higher frequency signal, and so at about 90-100 Hz a reduced current may be used, such as around 2-5 mA, for that patient.

Signal pulse width can also vary and be varied according to different patients and treatments. A pulse of duration up to 1 ms (milliseconds) is generally used. The duration, or width, can be less than this, and suitably is from 50-800 μs (microseconds) or from 100-600 microseconds, or less than 500 microseconds, suitably 450 microseconds or less. An apparatus of the invention has the pulse width set at about 250 microseconds, another is set at about 300 microseconds +/−50, with other parameters variable. Other apparatus can have an option for the patient to vary the pulse width.

In a specific embodiment, combining optional and preferred parameters as described herein, an apparatus generates a signal with pulse width approximately 250 microseconds, frequency 20-40 Hz, current 1-20 mA and duty cycle 50% over a 10 second period. Variation of these parameters in other embodiments of the invention is envisaged to accommodate variation of treatment modalities and patient physiologies.

To deliver the signal, one or more electrodes are used. Apparatus of the invention hence generally comprises two electrodes. These can be attached to the skin of the patient, on the face and/or neck, such as on either side of the jaw or neck, spaced apart. A separation of, say, 1 cm or more, or 3 cm or more, or 5 cm or more is generally used. Electrodes are conveniently attached so as to stay in place while the patient is sleeping while allowing the patient to move as normal in sleep. Adhesive surfaces on the electrodes are provided by conventional means, supplemented e.g. by use of gel, e.g. commercially available hydrogel, or more simply adhesive tape can be placed over the electrodes. Electrodes can be separated, at respective locations on the apparatus. Electrodes can be provided on a single electrode patch or zone of the apparatus, e.g. a combined electrode patch.

Electrodes can be connected to the power supply, e.g. external battery, by wires. In another embodiment a single unit comprises power supply and electrodes, for example a solid body may hold the power supply and have arms with electrodes mounted thereon or incorporated therein. In a specific embodiment, described in more detail below, an approximately V shaped body houses a battery pack to provide the power with electrodes located towards each end of the arms of the V. Adhesive surfaces on the electrodes then allow for easy attachment to the patient.

A further optional feature of the invention is to include within the apparatus the facility for modification of the signal, e.g. by the patient such as according to his or her appreciation of the signal suitable for treatment.

An apparatus of the invention accordingly may comprise one or more controls for adjustment of one or more signal parameters by the patient, for example the signal frequency, the signal current (by variation of applied voltage), the signal pulse width, the duration of the stimulation free period, or two or more or all such parameters.

The signal frequency is optionally adjustable, for example it can be adjusted by the patient between a choice of two or more or three or more frequencies, within any range disclosed herein. One specific embodiment has options of about 20 Hz, about 30 Hz and about 40 Hz. Another option is for the frequency to be variable continuously between upper and lower limits, say from about 20-40 Hz or from about 25-35 Hz.

The signal current is optionally adjustable, for example the signal can be adjusted by the patient between two or more or three or more current settings, again within any range disclosed herein. One specific embodiment allows adjustment of voltage across the electrodes to choose between a current achieved of about 5 mA, about 10 mA and about 15 mA, another allows choice between about 3 mA, about 6 mA and about 9 mA. A further embodiment allows choice between a current achieved of about 1.5 mA, about 3 mA, about 4.5 mA, about 6 mA, about 10 mA and about 15 mA. Another option is for the current to be variable continuously between upper and lower limits.

Referring to the specific embodiment described in more detail in the example, it is preferred that a patient can attach a relatively small and light, hence portable device for use overnight at home, without the need for a snoring or apnoea event monitor. Preferred embodiments of the invention are portable and can be worn on the patient; they do not include a monitor for snoring or sleep apnoea events as they deliver a continuous treatment during sleep. Preferred embodiments are lightweight and not cumbersome to wear. Specifically, they may weigh in total, including internal battery (if fitted) or external (meaning removable) battery, 150 g or less, preferably 100 g or less, more preferably 50 g or less. Specific embodiments made to date weight 30 g or less, and working examples have been made weighing approximately 20-25 g. Batteries are preferably rechargeable and an example has been made with a battery rechargeable wirelessly—between uses it is placed on an inductive charging module.

In a particular embodiment of the invention, and as described with more specific features in the example, there is provided a portable, battery powered apparatus that generates an electrical signal between electrodes to be applied to the skin of a patient for reduction or prevention of snoring or sleep apnoea, wherein the signal comprises electrical stimulation at a frequency of 1-100 Hz; and the signal comprises a stimulation free period of at least 0.5 seconds every 20 seconds.

Optional and preferred aspects of the apparatus and signal are as described more generally above in relation to the invention and more specifically below with reference to the specific example. The signal thus preferably may have a frequency of 5-60 Hz, separately may comprise a stimulation free period of at least 1 second every 10 seconds and may be capable of generating the signal for a period of 4 hours or longer, especially overnight. Advantages of the apparatus that apply in particular to portable versions include its cost effectiveness in providing satisfactory therapy and the lack of adverse treatment-related effects (especially compared to direct muscle/nerve stimulation) of the non-invasive approach. There can be minor skin irritation from wearing the pads but this can be reduced using creams or other treatments and by adjusting the precise pad positions on different nights. In testing of specific embodiments patients have found the apparatus easy to wear and use and have been able to adjust its settings to provide adequate therapeutic effect without disturbance to normal sleep patterns.

A still further feature of embodiments of the invention is that the power supply delivers a signal that ramps up from a low level, often zero, to the end strength signal over a period of time; this allows the user to fall asleep before the signal has reached full strength. In apparatus of such embodiments the signal delivered by the power supply comprises two phases, a first phase during which its strength gradually increases and a second, later phase during which the signal remains essentially the same strength. That second, treatment phase may continue for the remainder of the duration of treatment. The ramping phase delivers a reduced (though increasing) signal, making it easier to fall asleep without disturbance from the full strength signal.

The duration of the first phase may vary; it is suitably from about 5 to about 30 minutes. During this ramping phase, the signal may increase in strength by increase in the signal current or pulse width, or both. A prototype described below has a ramp of signal current over about 20 minutes.

Further provided by the invention is a method of treatment of snoring or sleep apnoea, comprising delivering via the skin of a patient a signal that stimulates the patient's tongue muscle, wherein the signal has a frequency of 1-100 Hz and is discontinuous so as to provide for continuous treatment without muscle fatigue.

The signal used in these methods is suitably as described elsewhere herein for, and suitably delivered using, the apparatus of the invention.

Hence, the method suitably comprises treatment using a signal that is discontinuous so as to provide the treatment without fatigue of the patient's tongue muscle being experienced such that the treatment fails to be effective. The signal of the treatment may be delivered, in other words the method may be continued, over a period of 3 hours or more, 4 hours or more, 5 hours or more, or for longer.

The method may use a signal that is discontinuous in that it comprises a stimulation free period of at least 0.5 seconds every 20 seconds. Optionally, the signal used has a frequency of 5-60 Hz. Optionally, the signal used has a current of up to 40 mA.

Other optional and preferred features of the device and the signal of the invention are optionally and preferably used in carrying out methods of the invention.

The invention is now described in specific embodiments in the following examples and with reference to the accompanying drawings in which.

Figure 1:
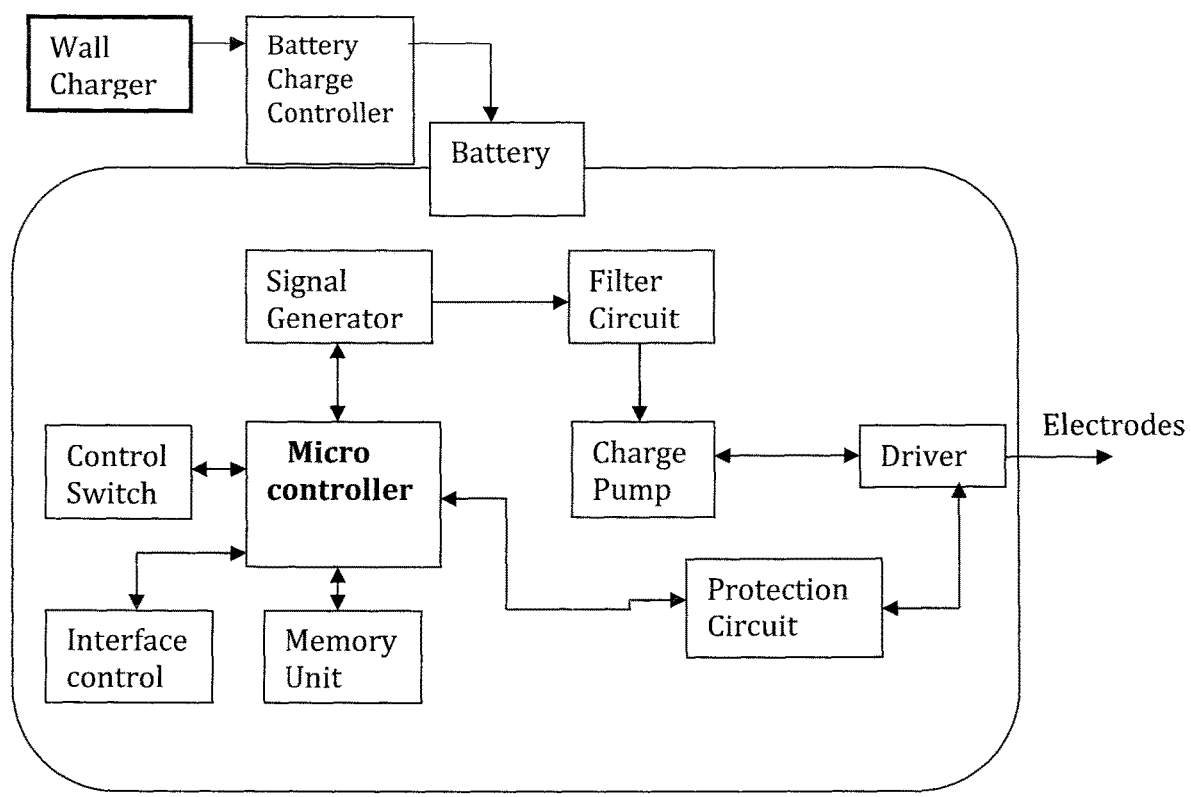
FIG. 1 shows a schematic circuit diagram of the power supply and electronics to generate the stimulation signal of the apparatus of the invention.
Figure 2:
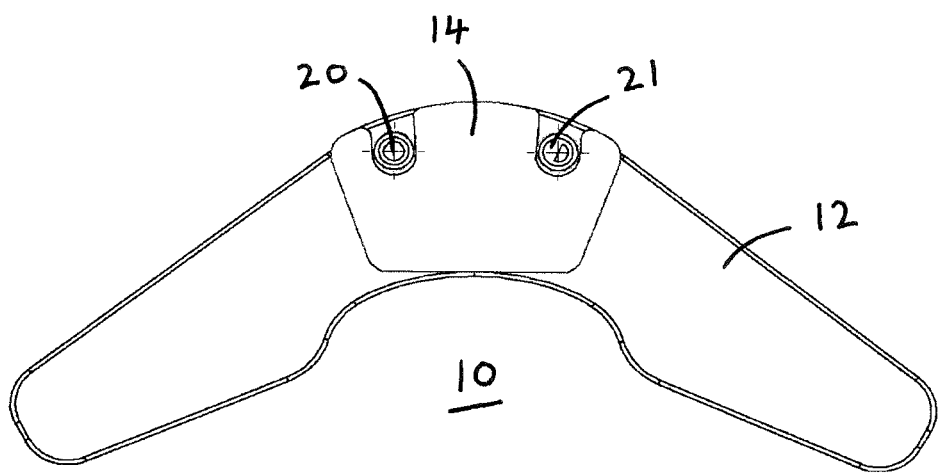
FIG. 2 shows a schematic view from underneath of an apparatus of the invention.
Figure 3:
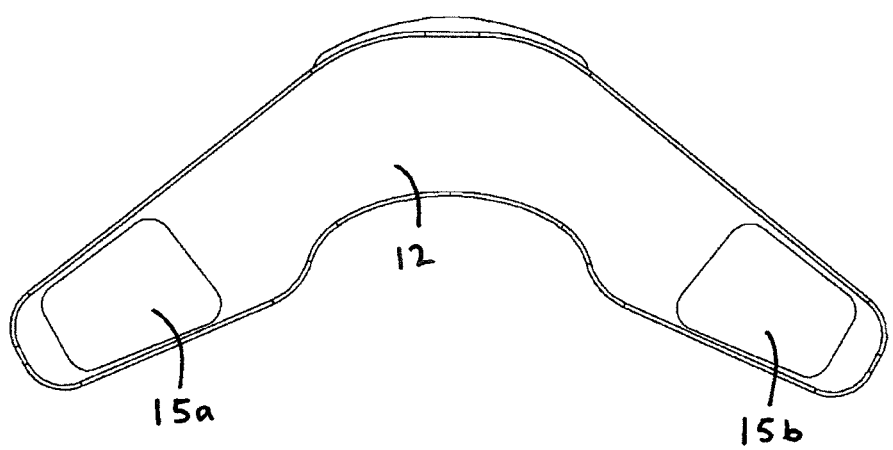
FIG. 3 shows a schematic view from above of the apparatus of FIG. 2.
Figure 4:
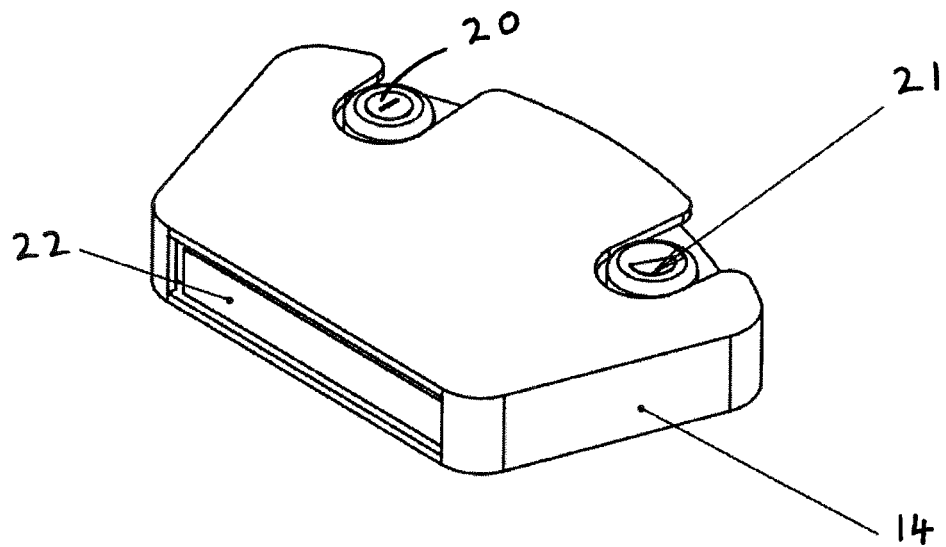
FIG. 4 shows a schematic view from below and to the side of the housing of the apparatus of FIG. 2.
Figure 5:
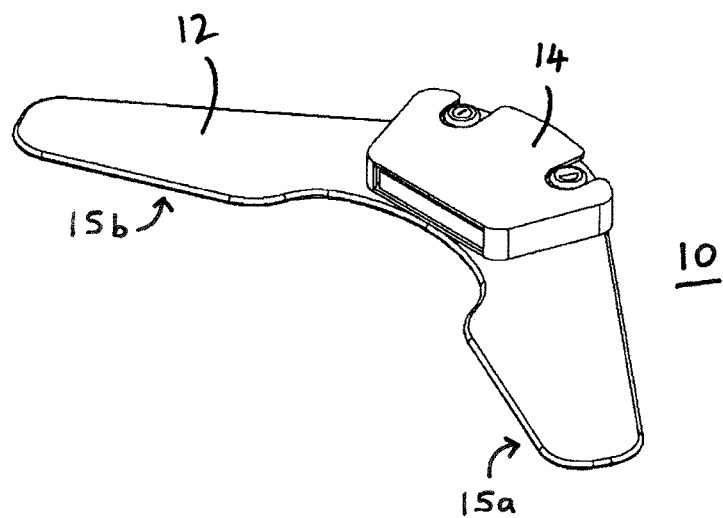
FIG. 5 shows a schematic view from below and to the side of the apparatus of FIG. 2.

Referring to FIG. 1, apparatus of the invention incorporates circuitry as schematically set out, designed to generate the stimulation signal described in the embodiments set out in detail below.

The battery charge controller is incorporated into a recharging cradle and can be plugged into the mains and receives the housing of the anti-snoring device to recharge its inbuilt rechargeable battery.

The unit incorporates a microcontroller that takes input from the switches allowing the user to change the settings mentioned earlier. The microcontroller generates the signals using the signal generator and controls other components. Memory provides the ability to store data for subsequent transfer to an external device for data analysis.

The filter circuit and the charge pump generate required waveforms which are then passed through a driver to control the power. The unit also has a protection circuit that monitors the output for enhanced safety.

Referring to FIGS. 2-7, the anti-snoring device shown generally as 10 has a V-shaped body 12 attached in its assembled form to housing 14 that holds the rechargeable battery and the printed circuit board incorporating the signal control circuitry illustrated schematically in FIG. 1.

On the body 12, electrodes 15a,b are located respectively on the two arms of the V, connected via connecting conductors (internal to the body, hence not shown) to body contact pads on the lower surface of the body (hence obscured by the housing in the figures). These pads correspond with and make contact within the assembled device to housing contact pads 18a,b on the housing 14. Hence, signal output from the housing driven by the circuitry and the battery is transmitted from contact pads 18a,b on the housing via contact pads on the body and the internal conductors in the body to the electrodes 15a,b for delivery to the patient.

Miscellaneous contact pads 19a,b,c,d on the housing 14 are for connection to the battery recharging cradle (via pads 19a,d) and for optional connection to an external computer interface for interrogation of data stored on the housing memory unit (via pads 19b,c). Other charging options, such as inductive charging can also be used.

Figure 6:
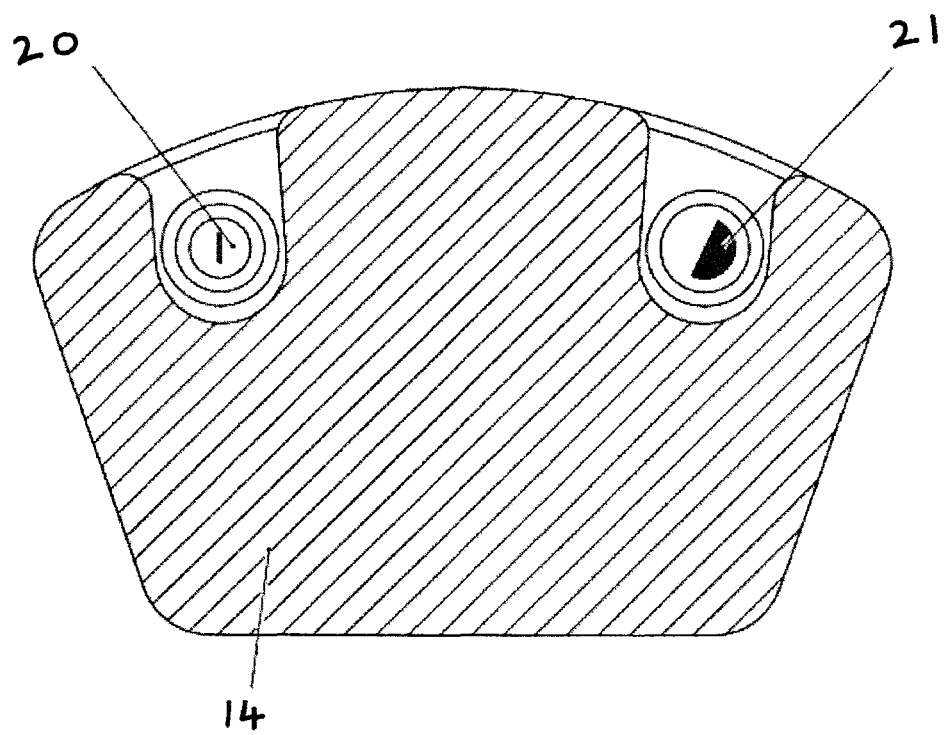
FIG. 6 shows a schematic view from below of the housing.
Figure 7:
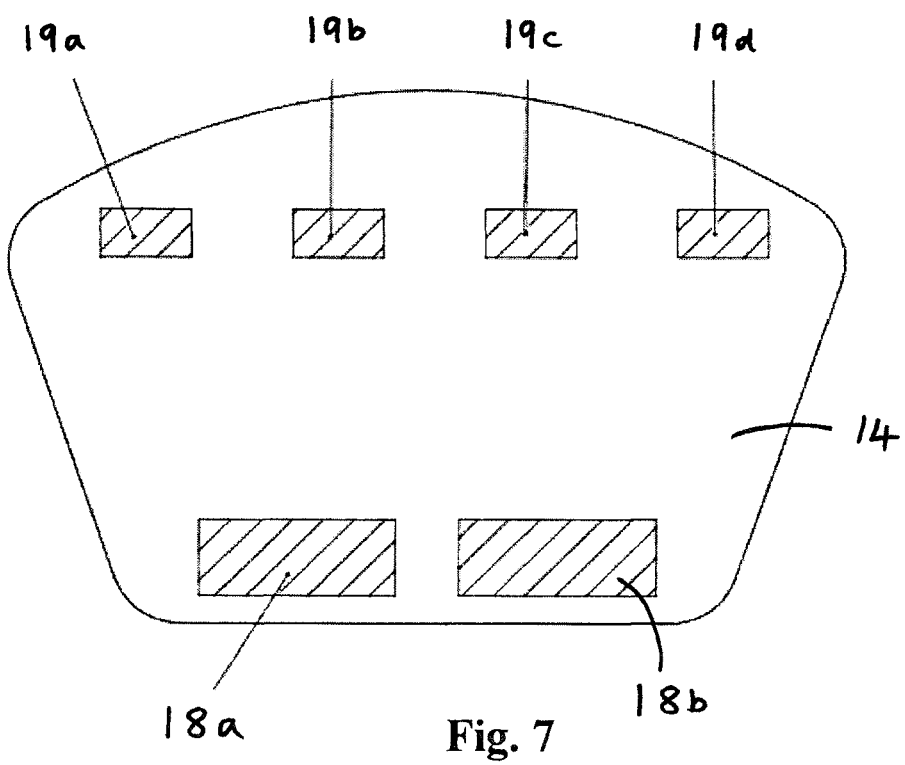
FIG. 7 shows a schematic view from above of the housing, illustrating housing elements that in the assembled device are directly connected to the body.

On the top surface of housing 14 are control buttons 20, 21. An on/off button 20 enables the patient to turn the device on and then off. The button further has in prototype A (see below) three positions for selection of different signal frequencies. In prototype B (again see below) there is no selection of signal frequency by the patient and this button has just an on/off function. Second control button 21 is provided on the right hand side as shown in FIG. 6 and has positions for control of current, with three positions available to the user in prototype A and seven in prototype B (see details below).

In use, a patient removes the detachable unit 22 from the charging unit cradle (not shown) and inserts it into the housing 14. Note that while some figures show separated components of the device, in use the device is a single unit as shown in fully assembled form in FIG. 5. For storage between uses the contact surfaces of electrode pads 15a,b are covered with removable, adhesive covers. The patient removes these by peeling them off, exposing tacky contact areas on the electrode pads. The connection between these pads and the patient can be maintained in day-to-day use by application of additional contact gel or by exchange of the adhesive covers.

The device is attached to respective left and right-hand sides of the underneath of the jaw and secured in place, optionally using adhesive tape or hydrogel adhesive if needed, with the pads sticking to and making electrical contact with either side of the jaw or just below.

The patient then turns on the device to a setting established from previous use. When being used for the first time, the patient turns on the device and then titrates its stimulation signal output to one suitable to that particular patient. In practice, the patient increases or decreases the signal current and increases or decreases the signal frequency (if control is available) to the point at which the stimulation is bearable and not so great as to prevent the patient falling asleep. One approach is to increase the current and/or frequency to the point at which the signal is not bearable by the patient and then turn it down to the point at which it is just bearable and will not prevent the patient falling asleep. Another approach is to turn the user variable elements to their minimum settings and then increase them one by one to the point at which the stimulation signal is just noticeable. For different patients, differing approaches to identifying a signal that is effective overnight and does not prevent restful sleep are taken. Once the apparatus is turned on and a particular setting chosen, the signal parameters are thus set. Over a period of approximately 20 minutes the voltage across the electrodes (giving the signal current) ramps up, i.e. gradually increases, from zero to the end voltage value. This allows for the patient to fall asleep before the signal has reached full strength, the level at which it will remain throughout sleep.

Between uses, the detachable unit is removed and can be recharged in the cradle. Simple assessment of the success of the device can be determined by whether the patient sleeps restfully without snoring. More complicated analysis can be carried out by downloading stored usage data from the housing via interface pads 19b,c and analysis e.g. by medically trained personnel.

The device settings for two developed prototypes are set out below. As will be appreciated, other devices are envisaged with alternative signal and device parameters and with alternative options for the user variable elements, as described more generally in the description above.

Specific details of 2 prototype devices that have been developed, with signal parameters and other internal features are as follows:

|  | Model | |
|---|---|---|
|  | Prototype A | Prototype B |
| Duty cycle | 50% | 30% |
| Time period for duty cycle | 10 s | 20 s |
| Pulse width | 250 μs | 300 μs |
| Current limit to the electrode pads | 1-20 mA | 1-20 mA |
| Signal frequency | 20-40 Hz | 30 Hz |
| Signal waveform | sinusoidal | square wave |
| Internal memory | RAM for internal log of usage data | |
| Maximum voltage at the pads | 80 v (+40/−40) | 80 v (+40/−40) |
| On/Off button | On housing | |
| Power supply | Internal rechargeable battery | |
| User variable elements | Signal frequency variable in 3 steps: 20 Hz, 30 Hz, 40 Hz; current variable in 3 steps: 3 mA, 6 mA, 9 mA | Current variable in 7 steps: 2 mA, 4 mA, 6 mA, 8 mA, 10 mA, 12 mA, 14 mA |

A separate battery charge unit is provided for connection to mains supply while not in use. Full charging takes 3-6 hours following typical overnight use.

Test of Anti-Snoring Device

A further prototype device of the invention was used in overnight trials to compare its effect on stimulated vs. control, non-stimulated patients.

The prototype was set up to deliver a pulse width of approximately 250 microseconds with a voltage adapted to deliver a signal current of about 4-8 mA, with frequency 30+/−2 Hz and duty cycle of 50%, with a substantially sinusoidal signal. A single prototype device was used for all patients.

Comparison between stimulated and non-stimulated patients indicated no severe adverse events in any patients as a result of use of the prototype.

Anti-Snoring Device with 6 Pre-Set Signals

A further prototype device of the invention was constructed with buttons allowing the user to turn the device on/off, by pressing a combination of both button 1 and button 2, and to cycle through 6 pre-set signals, by pressing button 1 to cycle up the settings and button 2 to cycle down the settings.

The signals were as follows:

| Parameter | Setting 1 | Setting 2 | Setting 3 | Setting 4 | Setting 5 | Setting 6 |
|---|---|---|---|---|---|---|
| Target current | 1.5 mA | 3 mA | 4.5 mA | 6 mA | 10 mA | 15 mA |
| Pulse width | 250 μs | 250 μs | 275 μs | 300 μs | 325 μs | 350 μs |
| Frequency | 30 Hz | 30 Hz | 30 Hz | 30 Hz | 30 Hz | 30 Hz |

After a set period of time, suitably around 1 minute, the buttons disable, ensuring that the settings cannot be adjusted accidentally during normal sleep. The requirement to press two buttons to switch the device on/off, opposed to just one, also prevents the user from disabling the device during normal sleep.

Accordingly, the present invention provides apparatus and a method for treatment of snoring and/or sleep apnoea.

The invention claimed is:

1. A portable, battery powered apparatus for treatment of snoring or sleep apnea in a patient comprising
a pair of electrodes, and
a power supply that generates an electrical signal between the electrodes to stimulate a patient's tongue muscle when the electrodes are attached to the patient,
wherein the signal comprises electrical stimulation at a frequency of 1-100 Hz;
wherein the signal is periodic and discontinuous so as to provide for continuous treatment without fatigue of the patient's tongue muscle,
wherein the apparatus does not comprise any monitoring functionality, and wherein the apparatus has a stimulation free period during which the apparatus applies no signal for at least 0.5 seconds every 20 seconds.

2. The apparatus of claim 1, which provides for said continuous treatment over a period of 3 hours or more.

3. The apparatus of claim 1, comprising a stimulation free period during which the apparatus applies no signal for at least 0.5 seconds every 10 seconds.

4. The apparatus of claim 1, comprising a stimulation free period during which the apparatus applies no signal for at least 1 second every 10 seconds.

5. The apparatus of claim 1, wherein the signal has a frequency of 5-60 Hz.

6. The apparatus of claim 1, wherein the signal has a current of up to 20 mA.

7. The apparatus of claim 1, wherein the signal comprises pulses of duration up to 1 ms.

8. The apparatus of claim 1, comprising one or more controls for adjustment of one or more signal parameters by the patient, selected from the signal frequency, the signal current, the signal pulse width, the duration of the stimulation free period, and two or more or all such parameters.

9. The apparatus of claim 8, wherein the signal frequency can be adjusted by the patient between three or more frequencies.

10. The apparatus of claim 8, wherein the signal can be adjusted by the patient between three or more current settings.

11. The apparatus of claim 1, wherein the signal delivered by the power supply comprises two phases, a first phase during which its strength gradually increases and a second, later phase during which the signal remains essentially the same strength.

12. The apparatus of claim 11, wherein the duration of the first phase is from about 5 to about 30 minutes.

13. The apparatus of claim 11, wherein during the first phase the signal current or pulse width increases.

14. A method of treatment of snoring or sleep apnoea, comprising delivering a single electrical signal that stimulates the patient's tongue muscle, wherein the single electrical signal has a frequency of 1-100 Hz and is discontinuous in that it comprises a stimulation free period of duration at least 0.5 seconds every 20 seconds so as to provide for continuous treatment without fatigue of the patient's tongue muscle such that the treatment fails to be effective,
wherein the method does not comprise monitoring the patient, the signal being delivered continuously with the stimulation free period, until stopped.

15. The method of claim 14, comprising delivering the signal of the treatment over a period of 3 hours or more.

16. The method of claim 14, wherein the signal has a frequency of 5-60 Hz.

17. The method of claim 14, wherein the signal has a current of up to 20 mA.

18. The method of claim 14, wherein the signal comprises a pulse of duration up to 1 ms.

19. The method of claim 14, wherein the signal is delivered using the apparatus of claim 1.

* * * * *